(12) United States Patent
Ina et al.

(10) Patent No.: US 6,410,797 B1
(45) Date of Patent: *Jun. 25, 2002

(54) PROCESS FOR THE PRODUCTION OF KETOISOPHORONE DERIVATIVES AND EQUIPMENT THEREFOR

(75) Inventors: Tomohide Ina, Himeji; Hiroyuki Miura, Takasago; Ikuo Takahashi, Kobe, all of (JP)

(73) Assignee: Daicel Chemical Industries, Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/623,081

(22) PCT Filed: Dec. 24, 1999

(86) PCT No.: PCT/JP99/07245

§ 371 (c)(1),
(2), (4) Date: Aug. 28, 2000

(87) PCT Pub. No.: WO00/40536

PCT Pub. Date: Jul. 13, 2000

(30) Foreign Application Priority Data

Dec. 28, 1998 (JP) ............................................ 10-372783
Dec. 21, 1999 (JP) ............................................ 11-362478

(51) Int. Cl.$^7$ .................................................. C07C 45/61
(52) U.S. Cl. ........................................ 568/344; 568/320
(58) Field of Search ................................ 568/344, 320; 422/189

(56) References Cited

U.S. PATENT DOCUMENTS

| 4,046,813 A | * | 9/1977 | Brenner |
| 4,845,303 A | | 7/1989 | Bellut |
| 5,545,761 A | * | 8/1996 | Dawson et al. |
| 5,874,632 A | * | 2/1999 | Hahn et al. |

FOREIGN PATENT DOCUMENTS

| EP | A2311408 | 4/1989 |
| EP | A2962252 | 12/1999 |
| JP | A4981347 | 8/1974 |
| JP | A5093947 | 7/1975 |
| JP | A51125315 | 11/1976 |
| JP | B2548650 | 4/1979 |
| JP | B2-5530696 | 8/1980 |
| JP | A61191645 | 8/1986 |
| JP | A1053553 | 2/1998 |
| JP | A1149717 | 2/1999 |
| JP | A-200034255 | 2/2000 |

OTHER PUBLICATIONS

Hosokawa et al., Chemistry Letters, pp. 1081–82 (1983).

* cited by examiner

Primary Examiner—Johann Richter
Assistant Examiner—Sikarl A. Witherspoon
(74) Attorney, Agent, or Firm—Birch, Stewart, Kolasch & Birch, LLP

(57) ABSTRACT

In the presence of an oxidizing catalyst, a β-isophorone derivative of the following formula (1) is oxidized in a solvent substantially from acid components (organic carboxylic acids) to form a ketoisophorone derivative of the following formula (2). The amount of the acid component in the solvent is 0 to 4,000 ppm (weight basis). The oxidizing catalyst is a complex salt of a transition metal and an N,N'-disalicylidenediamine. In the reaction, a cyclic base may further be employed as a co-catalyst. The solvent separated from the reaction mixture may be recycled to the oxidation reaction after removal of the acid component contained therein.

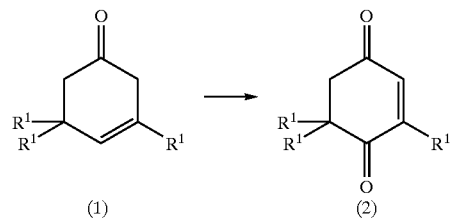

10 Claims, 2 Drawing Sheets

PROCESS FOR THE PRODUCTION OF KETOISOPHORONE DERIVATIVES AND EQUIPMENT THEREFOR

This application is the national phase under 35 U.S.C. §371 of PCT International Application No. PCT/JP99/07245 which has an International filing date of Dec. 24, 1999, which designated the United States of America.

1. Technical Field

The present invention relates to a process and an apparatus for producing ketoisophorone derivatives by oxidizing β-isophorone derivatives.

2. Background Technology

Ketoisophorone derivatives [e.g., 2,6,6-trimethylcyclohex-2-ene-1, 4-dione (ketoisophorone, KIP)] are useful intermediates for medicines, pesticides, perfumes, condiments, and polymer resins.

Japanese Patent Application Laid-Open No. 125316/1976 (JP-A-51-125316) discloses a method for producing an ethylenically unsaturated dicarboxylic acid (ketoisophorone) by oxidizing β-ethylenically unsaturated ketone (β-isophorone) with molecular oxygen or a molecular oxygen-containing gas in the presence of an inorganic or organic base and a cobalt or manganese chelate. In this literature, as the solvent, there are enumerated aromatic hydrocarbons, chlorinated aliphatic hydrocarbons, lower aliphatic alcohols, ketones, carboxyamides, nitriles, amines, and ethers.

In Japanese Patent Application Laid-Open No. 53553/1998 (JP-A-10-53553) discloses a method for producing ketoisophorone by oxidizing β-isophorone with molecular oxygen in the presence of a manganese complex salt and an organic base. In this literature, there are disclosed that the oxidation reaction is effected in the presence of water and that an organic acid, such as acetic acid and butyric acid, is added as an additive. Moreover, the use of a ketone (e.g., acetone, methyl isobutyl ketone) or an ether as the solvent is also described.

In these methods, however, certain of bases may sometimes lower the conversion of the substrate or selectivity considerably or cause β-isophorone to isomerize to α-isophorone. Particularly, when the concentration of β-isophorone in the reaction system is high (e.g., 20% by weight or more), the yield of ketoisophorone is significantly reduced. In these methods, if the reaction is repeated or performed continuously with the solvent circulating, high conversions and high selectivities are hardly kept.

β-isophorone can be prepared by isomerizing α-isophorone in the presence of an isomerizing catalyst composed of an acid. For example, in Japanese Patent Publication No. 8650/1979 (JP-B-54-8650) is disclosed a method for producing β-isophorone by the isomerization of α-isophorone in the presence of an isomerizing catalyst (an acid having a pK value of 2 to 5) followed by distillation.

Here, there may be proposed a process of producing ketoisophorone from α-isophorone by combining the isomerizing reaction and oxidizing reaction. The use of β-ketoisophorone obtained by the isomerization of α-isophorone, however, inhibits the oxidation reaction from efficiently proceeding, thus difficulty in producing ketoisophorone continuously.

As a process of producing ketoisophorone from α-isophorone, in Japanese Patent Publication No. 30696/1980 (JP-B-55-30696), Japanese Patent Application Laid-Open No. 191645/1986 (JP-A-61-191645), and Japanese Patent Application Laid-Open No. 93947/1975 (JP-A-50-93947) are disclosed methods of producing 4-oxoisophorone by oxidizing α-isophorone with oxygen in the presence of a catalyst. Japanese Patent Application Laid-Open No. 81347/1974 (JP-A-49-81347) discloses a method for producing 4-oxoisophorone by oxidizing α-isophorone with an alkaline metal chromic acid salt or a dichromate or a chromium trioxide. In the Chem. Lett. (1983), (7), 1081, there is proposed a method of producing 4-oxoisophorone by oxidizing α-isophorone with t-butylhydroperoxide in the presence of a palladium catalyst. However, in these methods, since the selectivity to ketoisophorone is low, separation of the by-product(s) formed or the metal catalyst and purification of the object compound are made complicated. Moreover, these methods sometimes involve the use of a heavy metal compound such as chromium which requires special treatment, or a peroxide which needs to be handled with care, leading to a decrease in working efficiency.

Thus, an object of the present invention is to provide a process and an apparatus for producing ketoisophorone derivatives at high conversions and high selectivities.

Another object of the present invention is to provide a process and an apparatus for continuously and efficiently producing ketoisophorone derivatives even in the case where β-isophorone derivatives obtained from α-isophorone derivatives are employed.

Still another object of the present invention is to provide a process and an apparatus for producing ketoisophorone derivatives without causing a reduction in conversion and selectivity even in the case of performing a reaction continuously with a solvent circulating.

DISCLOSURE OF INVENTION

The inventors of the present invention made intensive and extensive studies to achieve the aforementioned objects and found that, in an oxidation reaction of a β-isophorone derivative, an acid component present in the solvent in a very small amount adversely affects the catalyst, considerably deteriorating activity of the catalyst. The present invention is based on the above findings.

Thus, the process for producing ketoisophorone derivatives of the present invention comprises, in the presence of an oxidizing catalyst, oxidizing α-isophorone derivative represented by the following formula (1):

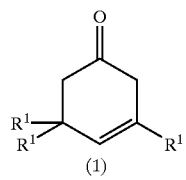

wherein the groups $R^1$ are the same or different, each representing an alkyl group, a cycloalkyl group, an aryl group, or a heterocyclic group in a solvent which contains substantially no acid component to form a ketoisophorone derivative represented by the following formula (2):

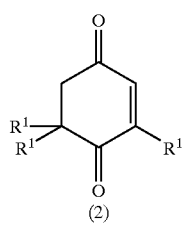

(2)

wherein the groups $R^1$ have the same meaning as defined above.

The amount of the acid component in the solvent is about 0 to 4,000 ppm (weight basis), and the solvent may be one treated with an alkali. The acid component is, for example, an organic carboxylic acid. A complex salt of a transition metal and an N,N'-disalicylidenediamine may be employed as the oxidizing catalyst. Optionally, a cyclic base may be used together as a co-catalyst. The solvent separated from the reaction mixture may be recycled for reuse in oxidizing β-isophorone derivatives after the acid component having been separated therefrom.

The present invention also includes an apparatus for producing ketoisophorone derivatives which comprises a removing unit for removing the acid component in the solvent, and a reactor for forming a ketoisophorone derivative of the formula (2) by, in the presence of an oxidizing catalyst, oxidizing a β-isophorone derivative of the formula (1) in the solvent supplied from the removing unit.

BEST MODE FOR CARRYING OUT THE INVENTION

Hereinafter, the present invention will be described in further detail with reference to the attached figures if necessary.

Figure 1:
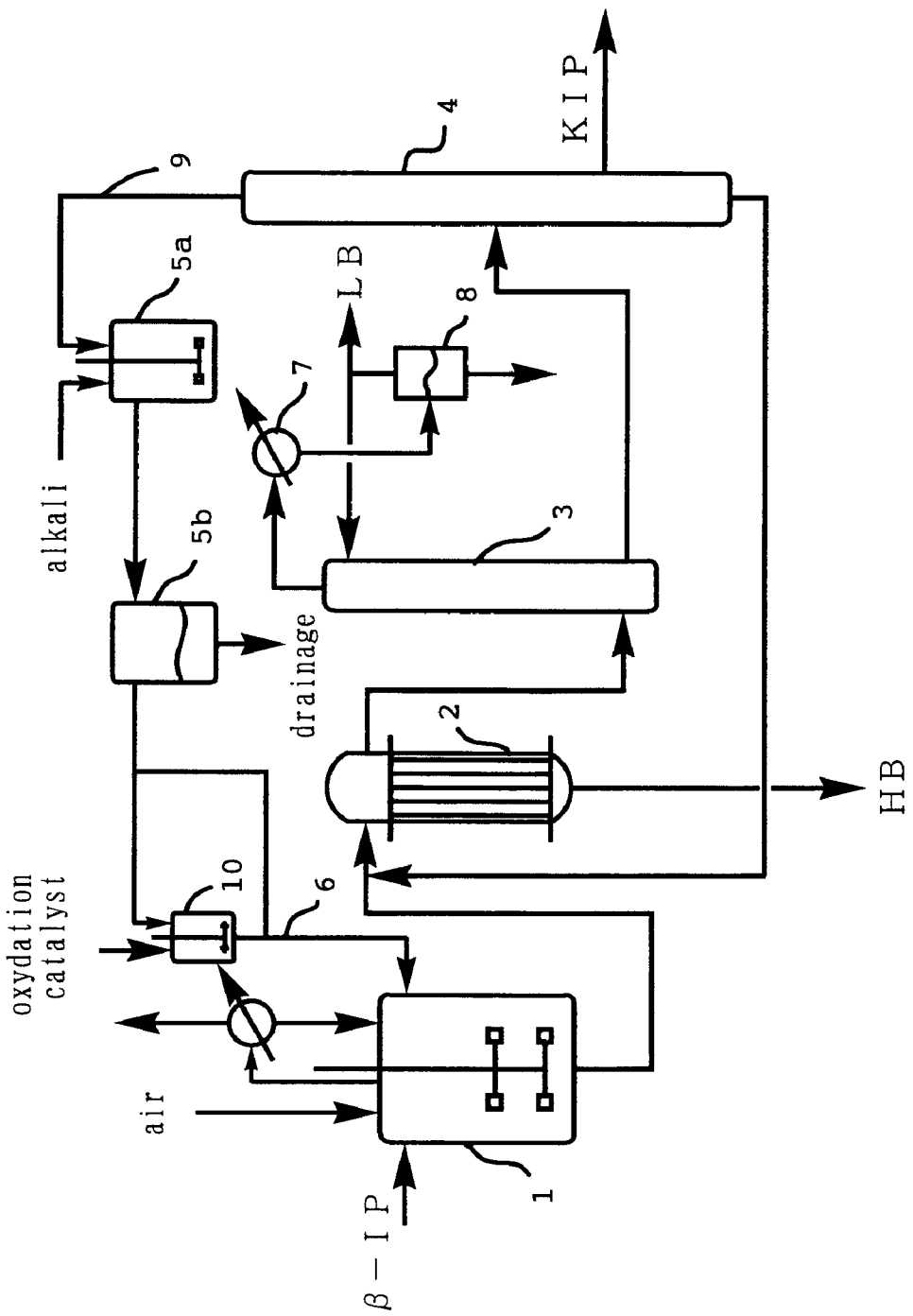
FIG. 1 is a flow chart illustrating the process and apparatus of the present invention.

FIG. 1 is a flow chart illustrating the process and apparatus of the present invention. In this embodiment, a β-isophorone derivative is oxidized in an oxidation reactor 1 to form a ketoisophorone derivative (oxidation step), and the ketoisophorone derivative thus formed is, through a separation system, continuously and successively separated and recovered from the reaction mixture formed in the reactor 1 (separation step). The separation system is composed of a distiller 2 for removing, among by-products, a high-boiling point component (HB) from the reaction mixture formed in the oxidation reaction; a distiller 3 for removing a low-boiling point component (LB) from the distillate came from the reactor 2; and a separation unit 4 for separating the resultant reaction mixture, which is drained from the bottom of the distiller 3 and no longer contains the low-boiling point impurities nor the high-boiling point impurities, into the ketoisophorone derivative and the solvent. Through a recycle line 9, the solvent separated by the separation unit 4 is supplied to an alkali-treatment unit 5a in which an alkaline aqueous solution to wash with is added to eliminate an acid component from the solvent. The mixture treated with the alkali is then fed to a liquid-separation unit 5b for separating the mixture into the solvent phase and the aqueous phase. On one hand part of the solvent from which the acid component has been removed(eliminated) by the liquid-separation unit 5b is recycled to the oxidation reactor 1 through a solvent-supply line 6 (recycling step) while on the other hand the rest of the solvent is supplied to a mixing vessel 10 through a branch line to be mixed with an oxidizing catalyst (oxidation catalyst). Thereafter, the catalyst-containing mixture prepared in the mixing vessel 10 merges with the solvent-supply line 6 and is fed to the oxidation reactor 1. Moreover, in this embodiment, the distiller 3 constituted of a distilling column is further equipped with a dehydration system composed of a cooling unit 7 and a liquid-separation unit 8 for eliminating the low-boiling point component. In the liquid-separation unit 8, the low-boiling component and water are separated from each other.

The β-isophorone derivative to be used in the present invention can be obtained by, in the presence of an isomerizing catalyst (e.g., acid catalysts), isomerizing an α-isophorone derivative shown by the following formula (3):

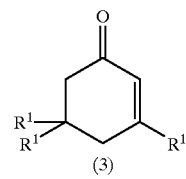

(3)

wherein $R^1$ has the same meaning as defined above [e.g., 3,5,5-tri$C_{1-4}$alkylcyclohex-2-ene-1-one (e.g., 3,5,5-trimethylcyclohex-2-ene-1-one (α-isophorone, α-IP))] and then distilling the β-isophorone derivative (2) thus formed under atmospheric pressure or reduced pressure (about 13 to 800 hPa (about 10 to 600 Torr)). As the catalyst for isomerization, organic carboxylic acids having boiling points higher than those of the α-isophorone derivative and β-isophorone derivative, such as $C_{4-12}$dicarboxylic acids (e.g., glutaric acid, adipic acid, suberic acid, sebacic acid), are available. The β-isophorone derivative formed by the isomerization is separated and purified batchwise, semi-batchwise, or continuously by distillation or other means, and then subjected to an oxidation step.

[Oxidation Step]

In the oxidation reactor 1, a ketoisophorone derivative of the formula (2) is formed by, in the presence of an oxidizing catalyst (oxidation catalyst), oxidizing a β-isophorone derivative of the formula (1) in a solvent containing substantially no acid component.

In the formulae (1) and (2), exemplified as the alkyl group designated by $R^1$ are $C_{1-10}$alkyl groups (e.g., $C_{1-8}$alkyl groups such as methyl, ethyl, butyl, isobutyl, t-butyl, pentyl, and hexyl). Examples of the cycloalkyl group are $C_{3-10}$cycloalkyl groups (e.g., cyclohexyl group). Exemplified as the aryl group are $C_{6-12}$aryl groups (e.g., phenyl group, substituted phenyl groups such as p-methylphenyl group). As the heterocyclic group, there are exemplified aromatic or non-aromatic 5- or 6-membered heterocyclic groups having at least one hetero atom selected from nitrogen, oxygen, and sulfur (e.g., furyl, thienyl, nicotinyl, pyridyl). Included among the preferred groups designated by $R^1$ are $C_{1-8}$alkyl groups, particularly $C_{1-6}$alkyl groups (e.g., $C_{1-4}$alkyl groups such as methyl and ethyl).

As the β-isophorone derivative (1), there are exemplified 3,5,5-tri$C_{1-4}$alkylcyclohex-3-ene-1-one (particularly, 3,5,5-trimethylcyclohex-3-ene-1-one (β-isophorone, β-IP)).

As the ketoisophorone derivative (2), there are exemplified 2,6,6-tri$C_{1-4}$alkylcyclohex-2-ene-1,4-dione [particularly, 2,6,6-trimethylcyclohex-2-ene-1,4-dione (ketoisophorone, KIP)].

The species of the oxidizing catalyst is not particularly restricted, and a complex salt (or a complex) of a transition metal and an N,N'-disalicylidenediamine or the like can be used. Such complex salt is useful in forming the ketoisophorone derivative (2) by oxidizing the β-isophorone derivative (1) with molecular oxygen.

As to the transition metal, the species or valence is not particularly restricted providing the transition metal can exercise its oxidation ability toward the aforementioned oxidation reaction, and at least one transition metal selected from the elements of the Groups 3 to 12 of the Periodic Table of Elements can be used. The valence of the transition metal may be divalent to octavalent, and is usually divalent, trivalent, or tetravalent. Examples of the preferred transition metal are the Group 5 elements (e.g., vanadium V, niobium Nb), the Group 6 elements (e.g., chromium Cr), the Group 7 elements (e.g., manganese Mn, rhenium Re), the Group 8 elements (e.g., iron Fe, ruthenium Ru), the Group 9 elements (e.g., cobalt Co, Rhodium Rh), the Group 10 elements (e.g., nickel Ni, palladium Pd), and the Group 11 elements (e.g., copper Cu). The preferred transition metal is, for example, V, Mn, Fe, Co, ,or Cu, with Mn particularly preferred. These transition metals can be used either singly or in combination.

The transition metal, together with an N,N'-disalicylidenediamine, can form a complex shown by the following formula (4a) or (4b):

and $C_{6-12}$ aromatic diamines such as diaminobenzene, diaminonaphthalene, biphenyldiamine; and derivatives thereof.

Included among the preferred N,N'-disalicylidenediamines are N,N'-disalicylidene $C_{2-8}$alkylenediamines (preferably, N,N'-disalicylidene $C_{2-5}$alkylenediamines) such as N,N'-disalicylideneethylenediamine ($H_2$ salene), N,N'-disalicylidenetrimethylenediamine, and N,N'-disalicylidene-4-aza-1,7-heptanediamine; and N,N'-disalicylidene $C_{6-12}$arylenediamines such as N,N'-disalicylidene-o-phenylenediamine, and N,N'-disalicylidene-2,2'-biphenylenediamine. Examples of the particularly preferred N,N'-disalicylidenediamine are N,N'-disalicylidene $C_{2-4}$alkylenediamines such as N,N'-disalicylideneethylenediamine ($H_2$ salene) and N,N'-disalicylidenetrimethylenediamine.

As the aromatic rings Z, there may be exemplified hydrocarbon rings (e.g., benzene, naphthalene) and heterocycles (e.g., nitrogen atom-containing heterocycles such as pyridine, pyrazine, pyrimidine, and quinoline; sulfur atom-containing heterocycles such as thiophene; and oxygen atom-containing heterocycles such as furan).

As to the substituents $R^2$ and $R^9$ of the aromatic rings Z, examples of the halogen atom are bromine, chlorine, and fluorine atoms, and examples of the alkyl group are $C_{1-6}$alkyl groups such as methyl, ethyl, propyl, butyl, and t-butyl groups. Examples of the alkoxy group are $C_{1-6}$ alkoxy groups such as methoxy, ethoxy, propoxy, and butoxy groups. Each of the substituents $R^2$ to $R^9$ is usually a hydrogen atom, a $C_{1-4}$ alkyl group, or a hydroxymethyl group.

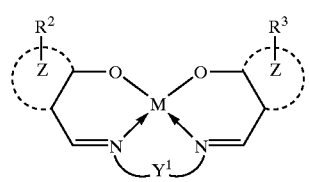

(4a)

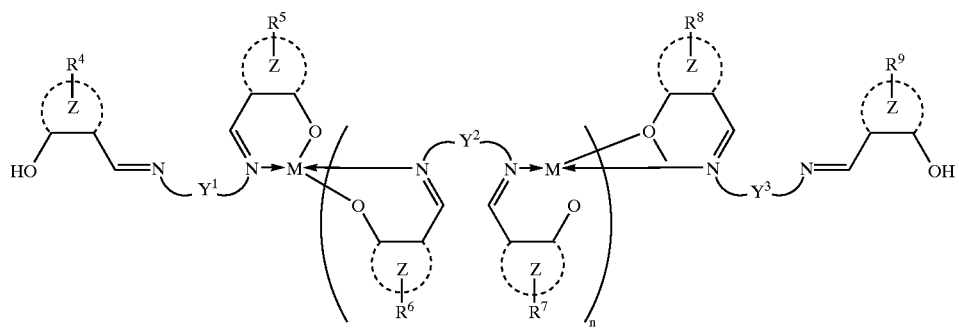

(4b)

wherein M stands for the transition metal; $R^2$, $R^3$, $R^4$, $R^5$, $R^6$, $R^7$, $R^8$, and $R^9$ are the same or different, each representing a hydrogen atom, a halogen atom, an alkyl group, or a hydroxyl group, an alkoxyl group, a hydroxymethyl group; $Y^1$, $Y^2$, and $Y^3$ are the same or different, each representing an alkylene group, a cycloalkylene group, or an arylene group; each ring Z stands for an aromatic ring; and n is 0 or an integer of 1 or more.

As diamines corresponding to the above $Y^1$, $Y^2$, and $Y^3$, there may be exemplified aliphatic diamines such as straight- or branched chain $C_{2-10}$ alkylenediamines and $C_{2-10}$ alkylenediamines containing an imino group (NH group); alicyclic diamines such as a diaminocyclohexane;

The complex may be amorphous, or crystalline like a compound represented by the formula (4b). In the formula (4b), n is 0 or an integer of 1 or more (e.g., 1 to 5, particularly 1 or 2).

In the above complex represented by the formula (4b), n+1 mol of N,N'-disalicylidenediamine is coordinated with n mol of the transition metal, and thus the complex is structurally different from a complex represented by the formula (4a) in which 1 mol of N,N'-disalicylidenediamine is coordinated with 1 mol of the transition metal. Moreover, in contrast to the complex (4a) which is amorphous, the complex (4b) is crystalline and shows a clear melting point when subjected to thermal analysis by TC/TDA. The melting point of the complex (4b) is usually about 190 to 240°

C. and particularly about 200 to 220° C. The complex (4a) and (4b) can be distinguished from each other by whether an absorption peak derived from the hydroxyl group is observed in the infrared absorption spectrum or not.

Included among the preferred complexes are complexes of manganese and N,N'-disalicylidene $C_{2-4}$alkylenediamines such as N,N'-disalicylideneethylenediamine ($H_2$ salene) and N,N'-disalicylidenetrimethylenediamine, particularly a complex of manganese and N,N'-disalicylideneethylenediamine (manganese-salene complex).

The above complex can be obtained by coordinating an excess of N,N'-disalicylidenediamine with a transition metal compound. As the transition metal compound, there may be exemplified organic acid salts (e.g., acetic acid salts), halides (e.g., manganese chloride), and inorganic acid salts. The ratio of the N,N'-disalicylidenediamine to the transition metal compound is the former/the latter (molar ratio)=about 0.5 to 5, preferably about 0.9 to 3, and particularly about 1 to 2. The reaction of the transition metal compound with the N,N'-disalicylidenediamine can be carried out in an inert solvent (e.g., an organic solvent such as alcohol). The reaction can be effected by stirring the reaction mixture in an atmosphere of an inert gas, usually at a temperature of from 70° C. to the ref lux temperature of the solvent.

The complex salt may be employed in combination with a nitrogen-containing compound as a co-catalyst to constitute a catalytic system. The nitrogen-containing compound contains at least one component selected from cyclic bases and non-cyclic bases. Preferred as the catalytic system is one constituted of (1) a combination of the complex salt or complex, and a cyclic base, (2) a combination of the complex salt or complex, a cyclic base, and a non-cyclic base, or (3) a combination of the complex and a non-cyclic base.

[Cyclic Base]

Exemplified as the cyclic base are alicyclic and aromatic bases having at least one (preferably, two) nitrogen atom.

The alicyclic bases include bases in which at least one nitrogen atom constitutes a hetero atom of the ring, for example, 5 to 10-membered monocyclic (mono-, heterocyclic) compounds such as pyrrolidine or derivatives thereof [N-substituted pyrrolidines (e.g., N-$C_{1-4}$ alkylpyrrolidines such as N-methylpyrrolidine), substituted pyrrolidines (e.g., 2- or 3-methylpyrrolidine, 2- or 3-aminopyrrolidine)], piperidine or derivatives thereof [N-substituted piperidines (e.g., N-$C_{1-4}$alkylpiperidines such as N-methylpiperidine; piperylhydrazine), substituted piperidines (o-, m-, or p-aminopiperidine)]; alkylene imines or derivatives thereof [hexamethylene imine, N-substituted hexamethylene imines (e.g., N-methylhexamethylene imine)], and piperazine or derivatives thereof [N-$C_{1-4}$alkylpiperazines such as N-methylpiperazine; N,N'-di-$C_{1-4}$alkylpiperazines such as N,N'-dimethylpiperazine; 2-methylpiperazine]; and poly-, heterocyclic compounds such as azabicyclo $C_{7-12}$alkanes (e.g., quinuclidine, 1,4-diazabicyclo[2.2.2]octane (DABCO), 1,5-diazabicyclo[3.2.1]octane, 1,5-diazabicyclo[3.3.0]octane, 1,4-diazabicyclo[4.2.0]octane, 1,5-diazabicyclo[3.3.1]nonane, 1,5-diazabicyclo[5.3.0]decane), azatricyclo$C_{8-16}$alkanes (e.g., 1,5-diazacyclo[3.3.0.0$^{2,6}$]octane, hexamethylenetetramine); and derivatives thereof.

Among these alicyclic bases, those containing at least two (particularly, 2 to 6) nitrogen atoms (e.g., polycyclic compounds (poly-, heterocyclic compounds) having a nitrogen atom at a bridgehead position) are preferable. Preferred as the alicyclic base is, for example, a 6 to 8-membered mono-, heterocylcic compound (e.g., piperazine, N-substituted piperazines, amino-substituted piperazines); an azabicyclo$C_{7-10}$alkane (e.g., quinuclidine, DABCO, or derivatives thereof); or hexamethylenetetramine.

Included among the aromatic bases are those having at least two nitrogen atoms in which at least one nitrogen atom constitutes a hetero atom of the ring. Examples of such aromatic base are aromatic heterocyclic compounds in which at least one nitrogen atom constitutes a hetero atom of the ring (e.g., pyridine) substituted with a substituent at least having a nitrogen atom (e.g., amino group, an N-substituted amino group) [N,N-di-substituted aminopyridines such as 2-, 3-, or 4-aminopyridine, 2-, 3-, or 4-mono- or di-alkylaminopyridines (e.g., di-$C_{1-4}$alkylaminopyridines such as dimethylaminopyridine), 2-, 3-, or 4-piperidinopyridine, and 4-pyrrolidinopyridine)]; pyrazine or derivatives thereof (e.g., 2-methylpyrazine); phthalazine, quinazoline, quinoxaline, or derivatives thereof; phenanthroline or its derivatives (e.g., 1,10-phenanthroline); and 2,2-bipyridyl or its derivatives, with N,N-di-substituted aminopyridines, pyrazine, phenanthroline, or derivatives thereof particularly preferred.

In the above cyclic base, a nitrogen atom(s) other than the one constituting the ring is preferably a tertiary amine, and the nitrogen atom as a hetero atom constituting the ring may be substituted with a substituent other than hydrogen atom. The cyclic bases can be used either singly or in combination.

The proportion (molar ratio) of the cyclic base to the complex is about 20/1 to 500/1, preferably about 30/1 to 300/1 (e.g., about 50/1 to 250/1).

[Non-cyclic Base]

As the co-catalyst, a non-cyclic base, such as a Schiff base, may be employed in conjunction with or in lieu of the cyclic base. Exemplified as the Schiff base are compounds having an imino bond or an anil bond. Schiff bases like these include, for example, compounds shown by the following formulae (5a) to (5h) and compounds having a similar structure.

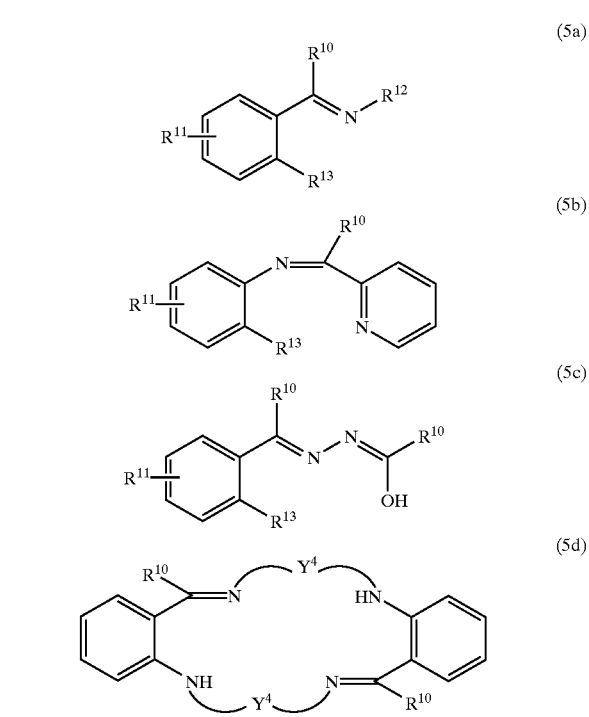

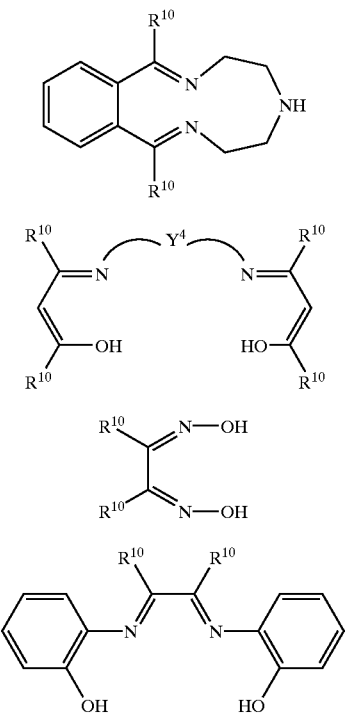

wherein $R^{10}$ and $R^{11}$ are the same or different, each representing a hydrogen atom, an alkyl group, an aryl group, or a cycloalkyl group; $R^{12}$ represents a hydroxyl group, an amino group, an alkyl group, oran aryl group; $R^{13}$ represents a hydroxyl group, an amino group, an alkyl group, an aryl group, or a pyridyl group; and $Y^4$ represents an alkylene group or a cyclohexylene group.

Exemplified as the groups designated by $R^{10}$ to $R^{12}$ and $Y^4$ are groups similar to those enumerated for $R^2$ to $R^9$ and $Y^1$ to $Y^3$.

Included among the preferred non-cyclic bases are salicylaldoxime, bisacetylacetone-ethylenediimine, di-methylglyoxime, diamine salicylaldimines as constituents of the complexes listed above (e.g., N,N'-disalicylidene$C_{2-5}$alkylenediamines such as N,N'-disalicylideneethylenediamine, N,N'-disalicylidenetrimethylenediamine and N,N'-disalicylidene-4-aza-1,7-heptanediamine), compounds having an imino bond such as bisimine compounds, and compounds having an anil bond such as glyoxal bishydroxyanil. N,N-disalicylidenediamines as constituents of the above complexes include, for example, ligands for the complexes shown by the formula (1).

When the non-cyclic base is used, the ratio (molar ratio) of the non-cyclic base to the complex is the former/the latter=about 0.1/1 to 20/1, preferably about 0.5/1 to 15/1 (e.g., 0.5/1 to 10/1), and usually about 1/1 to 10/1.

In the oxidation reaction, the amount of the oxidizing catalyst or co-catalyst relative to 1 mol of the β-isophorone derivative is as follows. Oxidizing catalyst: about $1 \times 10^{-5}$ to $1 \times 10^{-2}$ mol (preferably, $1 \times 10^{-4}$ to $1 \times 10^{-3}$ mol). Cyclic base: about $5 \times 10^{-2}$ to 1 mol (preferably, $1 \times 10^{-2}$ to 0.5 mol). Non-cyclic base: about $1 \times 10^{-5}$ to $5 \times 10^{-2}$ mol (preferably, $1 \times 10^{-3}$ to $5 \times 10^{-3}$ mol).

[Oxygen Source]

As the oxygen source for the oxidation reaction, compounds generating oxygen are also employable providing they are capable of supplying molecular oxygen as well as oxygen and oxygen-containing gases. As the oxygen source, although high-purity oxygen gases can be used, it is preferred that an oxygen gas diluted with an inert gas, e.g., nitrogen, helium, argon, or carbon dioxide is supplied to the reaction system. In the present invention, the β-isophorone derivative can be oxidized effectively even with air in lieu of oxygen as an oxygen source.

The concentration of oxygen in the oxygen source is, e.g., 5 to 100% by volume, preferably about 5 to 50% by volume, and particularly about 7 to 30% by volume. Even if the concentration of oxygen is as low as 8 to 25% by volume, the oxidation reaction proceeds effectively.

As to the way molecular oxygen is supplied to a reaction vessel or container, the reaction may be effected in a closed system previously supplied with sufficient molecular oxygen, or may be conducted with molecular oxygen continuously flowing. When allowing molecular oxygen to flow continuously, the flow rate is, for example, about 0.1 to 10 L/min and preferably about 0.5 to 5 L/min per unit volume (1 L).

[Reaction Solvent]

In the present invention, since a solvent which is substantially free from acid component (e.g., protonic acids having a pKa value of 5 or less, particularly organic carboxylic acids (e.g., $C_{1-10}$ loaliphatic carboxylic acids)) is employed, the ketoisophorone derivative (2) is produced at a high conversion and a high selectivity with maintaining a high activity of the oxidizing catalyst.

The source of the acid component cannot be determined exactly, but it may be ascribed to something decomposed in the oxidation reaction procedure. For example, the acid component may be ascribed to the solvent (e.g., diisobutyl ketone) decomposed in the oxidation reaction (e.g., decomposed into a $C_{1-10}$carboxylic acid, such as formic acid, acetic acid, isobutyric acid, isovaleric acid), or to a by-product (e.g., valeric acid, butyric acid) produced in the step of forming the starting material β-isophorone derivative (isomerization step of α-isophorone).

The amount of the acid component in the solvent is, e.g., about 0 to 4,000 ppm (weight basis), preferably about 0 to 2,000 ppm (weight basis), and more preferably about 0 to 900 ppm (weight basis).

There are no special restrictions on the choice of the solvent, provided that the solvent does not adversely affect or inhibit the reaction. A solvent phase-separable from water (or a solvent separable from water) such as a water-insoluble or hydrophobic solvent, particularly a non-water-miscible solvent, is usually employed, as the acid component in the solvent will later be removed by being washed with an alkali (e.g., an alkaline aqueous solution). As the solvent, there are exemplified aliphatic hydrocarbons such as hexane, heptane, and octane; aromatic hydrocarbons such as benzene, toluene, and xylene; alicyclic hydrocarbons such as cyclohexane; ketones (particularly, dialkyl ketones) such as methyl ethyl ketone and dibutyl ketones (e.g., dibutyl ketone, diisobutyl ketone, dit-butyl ketone); ethers such as diethyl ether, diisopropyl ether, dibutyl ether, tetrahydrofuran, dioxane, ethylene glycol monomethyl ether, ethylene glycol dimethyl ether, diethylene glycol monomethyl ether, and diethylene glycol dimethyl ether; halogenated hydrocarbons such as monochloroethane, dichloroethane, chloroform, carbon tetrachloride, and 1,2-dichloroethane; and esters such as methyl acetate, ethyl acetate, and butyl acetate. These solvents can be used either independently or in mixture. Preferred solvents include $C_{2-5}$alkyl-$C_{2-5}$alkyl ketones (particularly, dibutyl ketones).

A commercially available solvent also may be employed as the solvent to be used in the present invention. Also, the solvent once used for the oxidation reaction and recovered through the recycle line 9 may be sent back through the solvent supply line 6 to be reused. Usually, it is economical and advantageous to reuse the solvent recovered.

The concentration of the substrate in the reaction system is not particularly limited, but usually selected within the range of about 5 to 70% by weight, preferably about 15 to 60% by weight (e.g., 20 to 55% by weight).

The water content of the reaction system at the initial stage of the reaction can be selected freely unless the activity or other characteristics of the oxidizing catalyst are adversely affected, and is 1% by weight or less (about 0.001 to 1% by weight), preferably 0.5% by weight or less (0.001 to 0.5% by weight). A water content exceeding 1% by weight accelerates the reaction at its initial stage, but may cause the reaction to stop proceeding further or lower the selectivity to the ketoisophorone derivative. The reaction system contains not only the water present at the initial stage of the reaction but water produced by the reaction, and a finite amount of water is usually present in the present reaction system. Accordingly, the water present in the oxidizing reaction system (particularly, the water produced in the reaction) is separable and removable from the reaction system in the separation step which will later be described. The amount of water to be removed from the reaction system is at least 30% by weight, preferably at least 50% by weight, and more preferably at least about 80% by weight, relative to the total of the water generated.

The reaction temperature can be selected according to the reaction rate, selectivity, and a solvent to be used. To eliminate the risk of explosions, it is desirable that the reaction is conducted at a temperature lower than the flash point of the reaction solvent. For example, in the case of diisobutyl ketone (flash point: about 49° C.) employed as the solvent, the reaction can be effected at a temperature of about 35 to 45° C. Moreover, the reaction is usually carried out at atmospheric pressure, though possible to conduct at either atmospheric pressure or applied pressure (up to about 150 atm).

The reaction time (residence time in a flow reaction) is not particularly restricted, and usually about 0.5 to 30 hours (e.g., 1 to 10 hours).

In the oxidation step, there can be used a gas-liquid agitation-type oxidation reactor, and the amount of oxygen supplied and the conditions for stirring may sometimes affect the reaction selectivity. The preferred reactor is a reactor of high stirring efficiency, and such reactor may be equipped with a plurality of tiers (e.g., two tiers) of disc turbine rotor blades (e.g., 4 to 8 blades), and/or one or plural of buffle plates (e.g., 2 to 6 buffle plates). Further, oxygen may be supplied to the reaction system by being squirted in bubbles by a sparger. The stirring energy of the reactor per unit volume can be selected within the range of about 0.5 to 5 kw/m³ (preferably, 0.7 to 2.5 kw/m³).

The starting materials can be added to the reaction system in any order, and there is no particular restriction on the order of addition. However, for preventing the isomerization to an α-isophorone derivative, at an early stage of the reaction, it is preferred that the β-isophorone derivative is supplied to the reactor last, that is, after components (e.g., an oxidizing catalyst) other than the β-isophorone derivative has been fed to the reactor. Further, for inhibiting the generation of heat, the β-isophorone derivative may be continuously or intermittently supplied to the reaction system in drops, or in another way.

[Separation Step and Recycling Step]

In the separation step, using at least one purifying means (e.g., a distiller, a separator), the ketoisophorone derivative, the solvent, low-boiling point impurities, and high-boiling point impurities (e.g., oxidizing catalyst) are individually separated from the reaction mixture formed in the oxidation reaction. In the recycling step, using the alkali-treatment unit 5a and the liquid-separation unit 5b, the acid component is removed from the solvent separated in the separation step. The solvent is then circulated back to the oxidation step through the solvent-supply line 6.

[Separation of High-boiling Point Impurities (HB)]

The reaction mixture from the bottom of the oxidation reactor 1 is subjected to a first separation step for separating high-boiling point impurities, such as the oxidizing catalyst. This separation step may be carried out in a conventional manner, for example, using the distilling column 2 (particularly, a flash distiller). As the flash distiller, conventional ones, such as WFE (Wiped Film Evaporator) and FFE (Falling Film Evaporation), are available. Conditions under which a flash distillation is conducted depend on the species of the catalytic component, and the temperature is, for example, 80 to 150° C. (preferably 90 to 120° C.) and the pressure is about 13 to 133 hPa (10 to 100 mmHg) (preferably, 17 to 107 hPa (20 to 80 mmHg)). This distilling operation permits the recovery of the oxidizing catalyst from the bottom and the distillate mainly composed of theketoisophorone derivative, solvent, and low-boiling point impurities from the overhead.

The oxidizing catalyst recovered from the bottom of the distilling column 2 is directly, or after being regenerated (reactivated) if necessary, sent back to the oxidation step for reuse.

[Removal of Low-boiling Point Component (HB)]

The distillate collected from the overhead of the distilling column 2 is then subjected to a second separation step for removing low-boiling point impurities (e.g., reaction by-products). The low-boiling point component (impurities) includes products by-produced in the production step of the starting material β-isophorone derivative (isomerization step of α-isophorone) (particularly, decomposed products of the isomerizing catalyst), such as cyclic ketones, hydroxyl group-containing compounds (alcohols such as cyclic alcohols), and carboxyl group-containing compounds (carboxylic acids such as cyclic carboxylic acids). The boiling point of the low-boiling point component (impurities) is usually 100 to 180° C. (e.g., 100 to 160° C.), particularly 120 to 140° C.

The low-boiling point component(s) (impurities) can be removed by a conventional separating means, and condensation, distillation, extraction, or a combination means thereof may for example be adopted. Usually, the removal is carried out using a distilling column (or a rectifying column). The distilling column may be either a packed column or a plate column.

The low-boiling point component (impurities) may be removed in a single separation step or plural separation steps, or through a series of separation steps. In FIG. 1, when eliminating the low-boiling point component in a single separation step using a distilling column 3, the number of plates of the distilling column is not particularly restricted, and may for example be about 5 to 50 plates, preferably about 5 to 30 plates. The distilling operation can be performed at an overhead temperature of about 30 to 80° C. (preferably, about 30 to 70° C.), a bottom temperature of about 80 to 150° C. (preferably, about 100 to 130° C.) and at a pressure of about 17 to 267 hPa (20 to 200 mmHg)

(preferably, 53 to 200 hPa (40 to 150 mmHg)). The distilling operation can be conducted in a conventional manner, for example, by refluxing the solvent at a suitable reflux ratio (e.g., about 0.5 to 5, preferably about 1 to 3).

A combination of several separating steps is advantageous in separating water or the solvent from the low-boiling point component as well as the low-boiling point component from the reaction mixture. For example, the low-boiling point component and water can be removed simply through distillation (distilling column 3), but it is nevertheless more effective to remove the low-boiling point component and water by, if necessary, combining a cooling operation (using a cooling unit 7) of the low-boiling component distilled off and a separating operation of the liquid (using a liquid-separation unit 8) for eliminating the water contained in the low-boiling point component.

[Recovery of the Ketoisophorone Derivative]

From the bottom of the distilling column 3 is drained a bottom product containing the solvent and the ketoisophorone derivative but free from the high-boiling point component (HB) and low-boiling point component (LB). The bottom product (bottoms) containing the solvent is then subjected to a recovering step comprised of separation of the ketoisophorone derivative from the solvent and recovery of the ketoisophorone derivative, followed by a recycling step of recycling the solvent. The separation of the ketoisophorone from the solvent and the recovery of the ketoisophorone may be effected using a conventional purification means, such as a distilling column 4 (recovering column).

The number of plates of the distilling column (recovering column) may be about 10 to 80, and preferably about 20 to 50. The distilling operation may be performed at an overhead temperature of about 30 to 100° C. (preferably, 50 to 80° C.), a bottom temperature of about 120 to 200° C. (preferably, 150 to 180° C.), and at a pressure of about 7 to 133 hPa (5 to 100 mmHg) (preferably 13 to 67 hPa (10 to 50 mmHg)). The distillation may be performed in a conventional manner, for example, under reflux at a suitable reflux ratio (e.g., about 1 to 5, preferably about 1 to 3).

According to the boiling points of the ketoisophorone derivative and the solvent, although the keotoisophorone derivative may be distilled off from the overhead of the distilling column, the solvent, which boils at a temperature lower than the boiling point of the ketoisophorone derivative, is usually distilled off from the overhead. It is preferred that the ketoisophorone derivative is recovered by side-cut (e.g., at a plate at a height of 40 to 80% of the total number of the plates counted from the bottom).

From the bottom of the distilling column are discharged the remnants of the high-boiling point impurities (oxidizing catalyst) which the distilling column 2 was unable to remove. If necessary, the product from the bottom may be recycled to the distilling column 2 to be further separated into the high-boiling point impurities and the ketoisophorone derivative.

[Recycle of the Solvent]

Since the solvent separated from the ketoisophorone derivative (the solvent recovered) usually contains an acid component (e.g., organic carboxylic acids), the solvent is advantageously reused in the oxidation step when made substantially free of the acid component through removal.

A variety of physical and chemical techniques are available as ways of removing such acid component, and examples of which are adsorption and distillation. For removing the acid component efficiently, treatment of the solvent with an alkali is favorable. As the alkali-treatment, there are exemplified: a process of removing the acid component by bringing a solid alkaline component into contact with the solvent (by running the solvent through), and a process comprised of mixing an alkaline aqueous solution (or slurry) with the solvent and then separating the liquid (alkaline washing).

Figure 2:
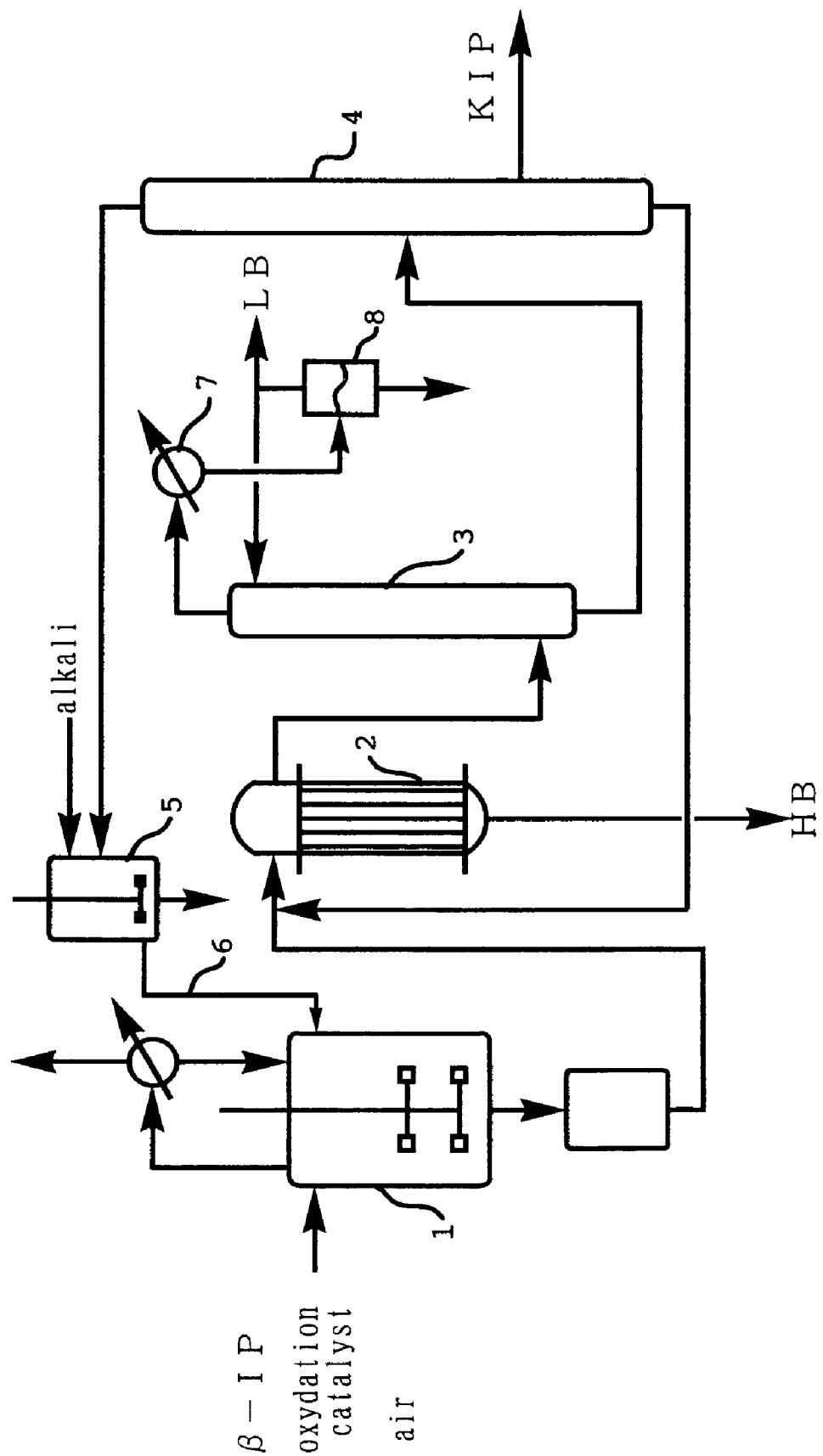
FIG. 2 is a flow chart illustrating another process and apparatus based on the present invention.

FIG. 2 shows another way of alkaline washing. In FIG. 2, an apparatus for producing ketoisophorone comprises: an oxidation reactor 1 for oxidizing a β-isophorone derivative to form a ketoisophorone derivative, a distiller 2 for removing high-boiling point impurities from the reaction mixture resulted from the oxidation, a distiller 3 for separating low-boiling point impurities from the distillate from the distiller 2, and a separation unit 4 for separating the ketoisophorone and the solvent from the reaction mixture from which the high-boiling point impurities and low-boiling point impurities have been removed. The solvent separated from the ketoisophorone in the separation unit 4 is fed to a removing unit 5 to be washed with an alkali. In the removing unit 5, the solvent is mixed with an alkaline aqueous solution (or slurry), and the mixture is then separated into phases to remove the acid component from the solvent.

Exemplified as the alkali for the alkali-treatment are hydroxides or salts of alkaline metals (e.g., lithium, sodium, potassium) or alkaline earth metals (e.g., magnesium, calcium), such as alkaline metal hydroxides (e.g., lithium hydroxide, sodium hydroxide, potassium hydroxide); alkaline metal hydrogencarbonates (e.g., lithium hydrogencarbonate, sodium hydrogencarbonate, potassium hydrogencarbonate); alkaline metal carbonates (e.g., lithium carbonate, sodium carbonate, potassium carbonate); alkaline earth metal hydroxides (e.g., magnesium hydroxide, calcium hydroxide); and alkaline earth metal carbonates (e.g., magnesium carbonate, calcium carbonate). Ammonium or an organic base (e.g., amines) may be used, if necessary. Preferred as the alkali is an alkaline metal hydroxide (e.g., lithium hydroxide, sodium hydroxide, potassium hydroxide).

As the alkaline aqueous solution (or slurry) with which to wash, an aqueous solution with a pH of 8 or higher is usually usable (preferably, a pH of 10 or higher).

Although the concentration of the alkaline aqueous solution (or slurry) can be selected within a wide range, it is usually selected within a range suitable in view of operability. For example, the concentration is about 10 to 90% by weight, preferably about 15 to 60% by weight.

If necessary, the concentration of the alkaline aqueous solution is adjusted to about 20 to 50% by weight, particularly to about 30 to 45% by weight. Useful components contained in the recovered solvent, such as the cyclic base (DABCO) and the non-cyclic base, are inhibited from being dissolved and removed with the alkaline aqueous solution by adjusting the concentration to such values.

The solvent from which the acid component has thus been removed is recycled to the oxidation reactor 1 through a solvent-supply line 6. If needed, the solvent thus recovered from which the acid component has been removed may be mixed together with an oxidizing catalyst in a mixer 10, and the resulting mixture is recycled to the oxidation reactor 1 through the solvent-supply line 6.

In the present invention, the oxidation reaction need only be effected in a solvent which is substantially free from acid components, and may be effected in a semi-batch system or batch system, as well as in a continuous system. For example, the apparatus illustrated in FIG. 2 may be used when producing ketoisophorone derivatives batchwise or semi-batchwise, while the apparatus shown in FIG. 1 is usually used when producing ketoisophorone derivatives in a continuous system.

The reaction solvent is not necessarily recycled.

The number of distilling columns to be employed in the distillation of the high-boiling point component, low-boiling point component, ketoisophorone derivative, or the solvent is not limited to one, and a plurality of distilling columns may be used if necessary. Although the distillation may be performed in batches, continuous distillation is industrially advantageous.

Moreover, as to the separation of the high-boiling point component (impurities) and low-boiling point component (impurities), inverse to the order of the steps and units described above, the oxidizing catalyst may be recovered after the removal of the low-boiling point component (impurities) followed by the high-boiling point component (oxidizing catalyst).

INDUSTRIAL APPLICABILITY

As was described above, in the present invention, since the oxidation reaction is effected using a solvent which substantially contains no acid component, ketoisophorone derivatives can be produced at high conversions and high selectivities. Particularly, the present invention realizes stable and continuous production of ketoisophorone derivatives from β-isophorone derivatives with efficiency. In addition, removal of an acid component by treatment with an alkali makes it possible to produce ketoisophorone derivatives without a deterioration in conversion and selectivity even if the reaction is continuously effected with the solvent circulating.

EXAMPLES

Hereinafter, the present invention will be described in further detail and should by no means be construed as defining the scope of the present invention.

Example 1

Using the apparatus shown in FIG. 1, a ketoisophorone derivative was produced through an isomerizing reaction and an oxidizing reaction in the following manner.

(1) Oxidation Step 0.92 g of manganese salene complex (Mn-salen) and 68 g of diazabicyclooctane (DABCO) were fed to a glass atmospheric oxidation reactor (volume: 10 L), and 1036.5 g of β-P and 3420.6 g of diisobutylketone (DIBK) were added thereto. The mixture was stirred with a disk turbine blade (100 mmφ) rotating at speed of 300 rpm for reaction while air is allowed to flow at 40° C. After being reacted for 5 hours, the reaction mixture was analyzed by gas chromatography, and it was found that 996 g of a ketoisophorone derivative (KIP) was formed at a conversion of 93% and a selectivity of 94%.

(2) Recovering Step of the Catalyst from the High-boiling Point Component

Using a stainless steel flash-distiller (WFE, Wiped film evaporator, 100 mmφ×height 200 mm), the reaction mixture was flash-distilled at a pressure of 53 hPa (40 mmHg) and a distilling rate of 600 g/hr to remove the manganese salene complex as the catalyst and high-boiling point component (HB) by-produced in the reaction, and a distillated composed of the reaction product KIP, the solvent DIBK, low-boiling point component (impurities), a co-catalyst DABCO, and an acid component (acetic acid) were distilled off as a distillate. The temperature of the distillate was 98° C. Z (3) Removing Step of the Low-boiling Point Component The distillate from the overhead of the distilling column 2 was supplied to a bottom of an oldershow distilling column (10 plates, 40 mmφ) equipped with a vacuum jacket at a supplying rate of 600 g/hr, and distilling off the low-boiling point component (LB) and water generated in the reaction while only the upper layer of the distillate was refluxed within the column at a pressure of 53 hPa (40 mmHg). The temperature of the bottom was 115° C., and the temperature of the distillate was 35° C.

(4) Recovery Step of KIP

The product (KIP, DIBK, co-catalyst DABCO, acid component) from the bottom of the oldershow distilling column mentioned above was supplied to the thirteenth plate from the top of an oldershow distilling column equipped with a vacuum jacket (30 plates, 40 mmφ) at a supplying rate of 600 h/hr, and distilled at a pressure of 40 hPa (30 mmHg) and a reflux ratio of 2.0 for separation-purifying KIP and DIBK. 956 g of KIP as a side-cut solution was collected at the 23th plate from the top. 1657 g of the distillate (DIBK, DABCO, acid component) from the overhead was supplied to a liquid-separation unit equipped with a stirrer, and the bottom product was fed to a flash-distiller. The temperature of the bottom was 162° C., the temperature of the side-cut plate was 131° C., and the temperature of the distillate was 74° C. Analysis of the separated solvent by gas chromatography showed that the concentration of the acid component (acetic acid) tobe 1,000 ppm (weight basis).

(5) Washing Step of the Solvent

The recovered solvent (DIBK) containing the acid component and DABCO distilled out from the overhead of the distiller, and 65 g of sodium hydroxide aqueous solution (40% by weight) were fed to the liquid-separation unit, and the mixture was violently stirred at room temperature (25° C.). After completion of the stirring, the lower layer (alkali layer) was separated to give DIBK substantially free of the acid component (acid component concentration: 0 ppm). The distribution ratio of the DABCO contained in the organic phase to that in the aqueous phase was: Concentration in the organic phase (weight %): Concentration in the aqueous phase (weight %)=1:0.08 Repeating the series of operations four times gave little or no influences over the activity the oxidizing catalyst showed in the oxidation reactions (conversion: 91%, selectivity: 95%). That is, its activity was kept high.

Comparative Example 1

Except that a solvent containing 5,000 ppm of an acid component (acetic acid) was used in the oxidation step, the same procedure was followed. Analysis of the reaction mixture by gas chromatography showed that a conversion to be 29% and a selectivity to be 81%.

Reference Example 1

97 g of the solvent in Example 1, recovered but not yet free of the acid component, and 3 g of sodium hydroxide aqueous solution were mixed and stirred. The distribution ratio of the contents of DABCO in the organic phase and the aqueous phase were determined. The results are shown in Table 1.

TABLE 1

| Sodium hydroxide aqueous solution concentration | Ratio (concentration in organic phase (wt %): concentration in aqueous phase (wt %) |
|---|---|
| 4 wt % | 1:0.23 |
| 13 wt % | 1:0.12 |

TABLE 1-continued

| Sodium hydroxide aqueous solution concentration | Ratio (concentration in organic phase (wt %): concentration in aqueous phase (wt %)) |
|---|---|
| 21 wt % | 1:0.04 |
| 39 wt % | 1:0.08 |

As was obvious from Table 1, the higher the concentration of the sodium hydroxide is, the lower the concentration of DABCO in the aqueous phase. In contrast to the aqueous phase, the concentration of DABCO in the solvent becomes increases.

What is claimed is:

1. A process for producing a ketoisophorone derivative, which comprises, in the presence of an oxidizing catalyst comprising a complex salt of an element of the Group 7 of the Periodic Table of Elements and an N,N'-disalicylidenediamne, oxidizing a β-isophorone derivative represented by the following formula (1):

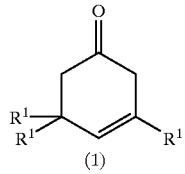

wherein the groups $R^1$ are the same or different, each representing an alkyl group, a cycloalkyl group, an aryl group, or a heterocyclic group in a solvent containing 0 to 4,000 ppm by weight of an acid component to form a ketoisophorone derivative represented by the following formula (2):

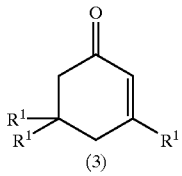

wherein the groups $R^1$ have the same meaning as defined above.

2. A process according to claim 1, wherein a solvent treated with an alkali is used as the solvent.
3. A process according to claim 1, wherein the acid component is an organic carboxylic acid.
4. A process according to claim 3, wherein the organic carboxylic acid is a $C_{1-10}$ aliphatic carboxylic acid.
5. A process according to claim 1, which further employs a cyclic base as a co-catalyst.
6. A process according to claim 5, wherein the co-catalyst is a polycyclic compound having a nitrogen atom at a bridgehead position.
7. A process according to claim 1, wherein the solvent is a ketone which is non-miscible with water.
8. A process according to claim 1, wherein the reaction is conducted, in the presence of an oxygen source, at a temperature lower than the flash point of the solvent.
9. A process according to claim 1, wherein an α-isophorone derivative shown by the following formula

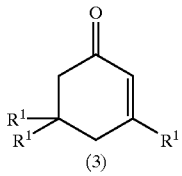

wherein each $R^1$ has the same meaning as defined above is isomerized in the presence of an acid catalyst to form the β-isophorone derivative.
10. A process according to claim 1, which comprises removing the acid component from the solvent separated from the reaction mixture, and recycling the resultant solvent to the oxidation reaction of β-isophorone derivatives.

* * * * *